United States Patent
Senegas

(10) Patent No.: US 12,347,142 B2
(45) Date of Patent: Jul. 1, 2025

(54) TOMOGRAPHIC IMAGING WITH MOTION DETECTION SYSTEM

(71) Applicant: KONINKLIJKE PHILIPS N.V., Eindhoven (NL)

(72) Inventor: Julien Senegas, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 564 days.

(21) Appl. No.: 17/635,014

(22) PCT Filed: Aug. 14, 2020

(86) PCT No.: PCT/EP2020/072830
§ 371 (c)(1),
(2) Date: Feb. 14, 2022

(87) PCT Pub. No.: WO2021/032606
PCT Pub. Date: Feb. 25, 2021

(65) Prior Publication Data
US 2022/0358676 A1 Nov. 10, 2022

(30) Foreign Application Priority Data
Aug. 22, 2019 (EP) .................................... 19193075

(51) Int. Cl.
*G06K 9/00* (2022.01)
*A61B 5/00* (2006.01)
(Continued)

(52) U.S. Cl.
CPC .............. *G06T 7/80* (2017.01); *A61B 5/1128* (2013.01); *A61B 5/721* (2013.01); *G06T 7/0012* (2013.01);
(Continued)

(58) Field of Classification Search
CPC ...................... A61B 5/721; G06T 2207/10072
See application file for complete search history.

(56) References Cited

U.S. PATENT DOCUMENTS 10,692,240 B2   6/2020  Mostafavi
10,984,241 B2   4/2021  Ota
(Continued)

FOREIGN PATENT DOCUMENTS

JP   2012108711 A   11/2010
JP   2014123193 A   12/2012
(Continued)

OTHER PUBLICATIONS

Ko, Youngjun, Jongduk Baek, and Hyunjung Shim. "3D motion artifact compenstation in CT image with depth camera." Image Processing: Machine Vision Applications VIII. vol. 9405. SPIE, 2015. (Year: 2015).*
(Continued)

*Primary Examiner* — Gregory A Morse
*Assistant Examiner* — Owais Iqbal Memon
(74) *Attorney, Agent, or Firm* — Larry Liberchuk

(57) ABSTRACT

A tomographic imaging system comprises a support carrying an image data acquisition system and defining a reference coordinate frame. A scan plan control sets the image-data acquisition system to acquire image-data from a selected imaging zone in the reference coordinate system. A motion detection system to detect movement and includes (i) a dynamic camera system to receive dynamic image information registered in the image coordinate frame of the dynamic camera system, (ii) an arithmetic unit configured to transform the selected imaging zone from the reference coordinate frame to the image coordinate-frame and a (iii) motion analyser to derive motion information from the registered dynamic image information in the transformed selected
(Continued)

imaging zone. In the event of motion detected by the motion analyser in or near the imaging zone, the detected motion may be employed for motion correction.

17 Claims, 3 Drawing Sheets

(51) Int. Cl.
  *A61B 5/11* (2006.01)
  *G06T 7/00* (2017.01)
  *G06T 7/254* (2017.01)
  *G06T 7/80* (2017.01)

(52) U.S. Cl.
  CPC .... *G06T 7/254* (2017.01); *G06T 2207/10072* (2013.01)

(56) References Cited

U.S. PATENT DOCUMENTS

| | | | |
|---|---|---|---|
| 12,042,306 B2 | 7/2024 | Senegas | |
| 2011/0201916 A1* | 8/2011 | Duyn | A61B 5/721 600/410 |
| 2012/0293667 A1* | 11/2012 | Baba | H04N 7/00 348/E17.002 |
| 2013/0345543 A1 | 12/2013 | Steibel et al. | |
| 2015/0077113 A1 | 3/2015 | Benner | |
| 2015/0196780 A1 | 7/2015 | Tijs et al. | |
| 2016/0055675 A1 | 2/2016 | Kasahara et al. | |
| 2016/0367169 A1* | 12/2016 | Hardie | A61B 5/743 |
| 2017/0143271 A1 | 5/2017 | Gustafsson et al. | |
| 2018/0014745 A1 | 1/2018 | Senegas et al. | |
| 2018/0014746 A1* | 1/2018 | Harrington | A61B 17/3207 |
| 2018/0249927 A1 | 9/2018 | Ernst et al. | |
| 2021/0052243 A1* | 2/2021 | Don | A61B 6/4417 |

FOREIGN PATENT DOCUMENTS

| | | |
|---|---|---|
| WO | 2013094366 A1 | 6/2013 |
| WO | 2015093130 A1 | 6/2015 |

OTHER PUBLICATIONS

J. Maclaren, M. Aksoy, and R. Bammer. Contact-free Physiological Monitoring Using a Markerless Optical System. Magn Reson Med. 2015; 74(2):571-577.

J.Y. Cheng, J. Lu, G. Scott et al. Optical Motion Monitoring for Abdominal and Lung Imaging. ISMRM 2017, #3936.

G. Farneback. Two-frame motion estimation based on polynomial expansion. In Image Analysis, pp. 363-370, Springer, 2003.

International Search Report and Written Opinion from PCT/EP2020/072830 mailed Dec. 16, 2020.

* cited by examiner

TOMOGRAPHIC IMAGING WITH MOTION DETECTION SYSTEM

CROSS REFERENCE TO RELATED APPLICATIONS

This application is a U.S. national phase application of International Application No. PCT/EP2020/072830 filed on Aug. 14, 2020, which claims the benefit of EP Application Serial No. 19193075.9 filed on Aug. 22, 2019 and is incorporated herein by reference.

FIELD OF THE INVENTION

The invention pertains to a tomographic imaging system with a motion detection system.

BACKGROUND OF THE INVENTION

Such a tomographic imaging system is known from the US-patent application US2011/0201916.

This known tomographic imaging system is configured to obtain MRI images concurrently with images obtained with a camera. The images obtained with the camera are correlated with the MRI images, resulting in motion correction data.

SUMMARY OF THE INVENTION

An object of the invention is to provide a tomographic imaging system that has a more reliable motion detection system.

This object is achieved by the tomographic imaging system comprising:
- a support carrying an image-data acquisition system and defining a reference coordinate-frame,
- a scan plan control to set the image-data acquisition system to acquire image-data from a selected imaging zone in the reference coordinate system,
- a motion detection system to detect movement and including
  - a dynamic camera system to receive dynamic image information registered in the image coordinate frame of the dynamic camera system
  - an arithmetic unit configured to transform the selected imaging zone from the reference coordinate frame to the image-coordinate-frame,
  - a motion analyser to derive motion information from the registered dynamic image information in the transformed selected imaging zone.

The tomographic imaging system of the invention is for example a magnetic resonance examination system, a computed-tomography (CT) system, an x-ray imaging system or a nuclear medicine imaging system. Such a tomographic imaging system comprises a gantry that forms the support carrying e.g. the x-ray source and x-ray detector of the computed tomography system, or the support carrying the main magnet of the magnetic resonance examination system. Other examples of tomographic imaging systems in which the invention may be incorporated are nuclear medicine tomography systems such as positron emission tomography (PET) systems, single-photon emission computed tomography (SPECT) systems and also hybrid tomography systems, such as PET-CT systems and MRI-CT systems. The invention may also be incorporated in tomographic image guided radiotherapy systems, such as MR-LINAC systems. The support defines a reference coordinate-frame. Tomographic image data (e.g. attenuation profiles or k-space profiles) are acquired in the reference coordinate-frame. The scan plan control is configured (e.g. in software) to set the image-data acquisition system to acquire the tomographic image data from a selected imaging zone in the reference coordinate-frame, in which e.g. a part of the anatomy of a patient to be examined is positioned. The selected imaging zone may be set on the basis of user input to the scan plan control or may be applied to the scan plan control on the basis of region recognition from an earlier survey image.

The motion detection system is camera-based and includes a dynamic camera system to receive dynamic image information from the camera-range of the camera system. The camera range is the volume for which the camera system is sensitive to obtain the dynamic image information from, i.e. the field-of-view of the dynamic camera system. The dynamic image information of the camera system is registered in the camera system's image coordinate-frame, i.e. in the proper coordinate-frame of camera's image sensor (i.e. in image pixel coordinates). When the dynamic camera system is mounted on the support, then inherently there is a defined geometric transformation between the reference coordinate-frame and the camera system's image coordinate-frame. This transformation derives from the system's geometry; this may contain moving parts, like a patient support or rotating gantry and the geometric transformation may account for these variations of the system's geometry. When the dynamic camera system is not fixedly mounted to the support, then upon setup of the dynamic camera system a calibration of the geometric transformation between the reference coordinate-frame and the image coordinate-frame may be required.

The selected imaging zone is defined in the reference-coordinate system and is reliably and robustly and stable geometrically related to the image coordinate-frame of the camera system. Notably, the geometric transformation may be a 3D-to-2D projection from the three-dimensional volume of the reference coordinate-frame onto the two-dimensional area of the image coordinate-frame of the camera system. By way of the geometric transformation, the selected imaging zone can be transformed onto the image coordinate frame, yielding a transformed selected imaging zone in the image coordinate-frame of the camera system. In other words, the selected imaging zone is projected as a region-of-interest onto the image pixel coordinates of the image coordinate-frame.

The motion analyser is configured to derive motion from the dynamic image information acquired by the camera system from within the region-of-interest transformed from the selected imaging zone. This enables to determine if motion takes place within or near the imaging zone; the imaging zone being defined in the reference coordinate-frame of the support. The motion analyser is configured to recognise changes of objects of features in the dynamic image information from the dynamic camera system. Such motion in or near the imaging zone may disturb image information acquired by the image-data acquisition system, e.g. in that motion corruption may confound computed-tomography attenuation profiles acquired by an x-ray detector or k-space profiles acquired by the magnetic resonance examination system's the RF-receiver system. Accordingly, in the event of motion detected by the motion analyser in or near the imaging zone, the detected motion may be employed for motion correction of the image information, or in the reconstruction of a final image from the acquired image information. On the other hand, the imaging procedure is not disturbed by motion picked-up by the dynamic camera system and that occurs beyond the imaging zone and which motion does not take place in the imaging zone and needs not to be corrected for.

The support (i.e. the gantry) defines the examination zone, notably the region around which the x-ray source and x-ray detector may rotate or the bore of the magnetic resonance examination system. The examination region is the space in which a subject to be imaged, i.e. patient to be examined may be positioned. During tomographic imaging data profiles (x-ray attenuations, k-space profiles) are acquired from a subject to be imaged (patient to be examined) in the examination zone. The imaging zone defines the volumetric region of the subject from which data profiles are to be acquired for reconstruction of the tomographic image(s). From these profiles tomographic images (e.g. computed tomography images or magnetic resonance images) may be reconstructed. These profiles are acquired from a portion of the anatomy, i.e. in the selected imaging zone, of the patient to be examined. The reconstructed image is applied to the output of the tomographic imaging system. The reconstruction of the magnetic resonance image from the acquired k-space profiles or attenuation profiles may be done on board of the tomographic imaging system. Alternatively the reconstruction may be outsourced to a reconstruction facility that is in on-line correspondence with the tomographic imaging system. That is, acquired profile data and optionally also the motion correction data may be uploaded to a reconstruction facility e.g. in the cloud and motion correction as well as image reconstruction can be done by the off-site reconstruction facility and the reconstructed image date returned to the user, e.g. to the tomographic imaging system or to a separate workstation.

In a further detailed embodiment of the invention, the motion detection system may access a volumetric outline of the subject to be imaged. The volumetric outline may be represented by an image dataset and represents the three-dimensional outer surface of the subject in the reference coordinate frame. The subject is e.g. (a part of) the body of the patient to be examined.

By way of the scan plan control, the imaging zone to be tomographically imaged by the tomographic imaging system may be selected in the reference coordinate-frame. The selection may be done automatically based on instructions what part of the subject is to be examined or the selection may be done manually. The scan plan control may be implemented in software and may be user controlled via a graphic user interface at which the user may indicate the selection that is then planned to be imaged.

The region-analyser is configured to determine in the reference coordinate/frame (a) zone(s) of interest of the volumetric outline in the selected imaging zone. The region-analyser is implemented in software that is capable of registering the volumetric outline and the selected imaging volume in the reference coordinate-frame. The arithmetic unit is further configured to transform the portions of interest onto the image coordinate-frame of the dynamic camera system. This defines a the region-of-interest in the image coordinate-frame for the motion detection system to be used for motion analysis.

The dynamic camera system is set to acquire the dynamic image information from the zone-of-interest in the reference coordinate-frame. In that way the dynamic camera system may capture movements in its range that may include (part of) of the selected imaging zone. The motion analyser derives the motion only or predominantly from the region-of-interest, while the dynamic camera system may also image outside of the examination region. With predominantly shall be understood that in certain cases the motion analyser may include data taken from a region slightly larger than the region-of-interest (e.g. 1%, 3%, 5% or 10% larger in one or more dimension) in order to capture also motion just outside selected imaging zone, as these movements may still have some effect on the images acquired by the tomographic system.

The location and size of the acquisition range of the dynamic camera system may be adjusted on the basis of the determined portion of the zone-of-interest in the volumetric outline in the image coordinate-frame so that the dynamic image information predominantly relates to motion of the portions of interest. Hence, the dynamic image information is a proper basis for detection of motion that actually matters for motion correction of the tomographic image information. The detection of motion may done by a software implementation of the motion analyser that may compare successive image frames of the dynamic image information to detect that a feature in the image information has moved. Any motion that may be in the range of the dynamic camera system but not in the (imaging) zone of interest is avoided in motion correction of the tomographic image information. That is, any motion that may be in the range of the dynamic camera system, but not or unlikely to be confounding the image quality of the tomographic image, will not be taken into account for motion detection. Accordingly, a more reliable motion detection is achieved.

The invention obviates the need to (e.g. manually) restrict the camera range to the imaging zone and its close surroundings.

These and other aspects of the invention will be further elaborated with reference to the embodiments defined in the dependent Claims.

In a preferred example of the tomographic imaging system of the invention, the support's inherent coordinate system is employed as the reference coordinate-frame. The support's inherent coordinate system may be the coordinate system defined by the magnet structure defining the magnet bore or the mounting support carrying the x-ray source and x-ray detector. Alternatively, the reference coordinate-frame may be defined relative to another component of the tomographic imaging system that is well-defined. In one example the reference coordinate-frame may be linked to the patient carrier. Then the reference-coordinate-frame moves with the patient carrier and the geometric transformation on the image coordinate frame will take into account the movement of the patient carrier relative to the dynamic camera system. In this way the reference coordinate-frame is practical and relates directly to the examination region.

In a practical example of the tomographic imaging system, the dynamic camera system is mounted to the support, such that its imaging range covers the location of the subject or even at least the whole of the examination region. Hence, the dynamic camera may be used to monitor the situation in the examination zone, not only for motion but e.g. also for localisation of auxiliary equipment and to be able to view the patient to be examined while in the examination region.

In a further practical example of the tomographic imaging system, a separate depth camera is provided to acquire the volumetric outline. The depth camera may be mounted such that the volumetric outline may be acquired while the subject (e.g. patient to be examined) is outside of the examination region. The depth camera is also calibrated to the coordinate frame of the support. In another embodiment the dynamic camera system is configured to also acquire the volumetric outline.

In yet another example, the volumetric outline may be acquired by the tomographic imaging system itself. Alternatively, the volumetric outline may be derived from a previous tomographic (e.g. MR or CT) examination, with the data being accessed from a PACS system. In the case of the magnetic resonance examination system the volumetric outline may be derived from a survey scan of magnetic resonance signals at relative low spatial resolution. In the case of the computed tomography system the volumetric outline may be acquired from attenuation profiles at low x-ray dose and coarse spatial resolution.

In a further implementation the volumetric outline is registered in the reference coordinate-frame of the support. In this way the volumetric outline may be acquired in a reference frame that is independent from the coordinate system of the dynamic camera system. For example the volumetric outline may be acquired by the depth camera mounted to view a region outside of the examination region.

The invention also pertains to a method of motion detection, According to the method of the invention the volumetric outline of the subject to be topographically imaged is accessed (from a memory) or has been acquired e.g. by a depth camera. The imaging zone of interest that is to be tomographically imaged is planned. This planning may be done automatically on the basis of instruction what part is to be imaged, or may be done manually by way of a user interface that shown e.g. already acquired survey image information. During tomographic image acquisition also dynamic image information is acquired, e.g. by way of the dynamic camera system. The volumetric outline and the imaging zone are registered in the imaging coordinate-frame of the support of the tomographic imaging system. The dynamic image information is registered in the reference coordinate-frame of the dynamic camera system. In the reference coordinate-system, the overlap of the volumetric outline with the imaging zone is determined. This overlap is geometrically transformed onto a region-of-interest in the image coordinate-frame from the reference coordinate-frame The geometrical transformation of points in the 3D overlap onto the 2D image coordinate-frame is a projection that may be determined by calibrating the dynamic camera system to the reference coordinate frame in which also the tomographic image data are acquired by the tomographic imaging system. Then the parts of the volumetric outline that are in the region-of-interest are monitored for motion by the dynamic image information. That monitored motion may be particular of interest to correct the tomographic image data for motion effects. The motion correction for motion detected within the region-of-interest may be employed to correct the k-space profiles or the attenuation profiles. Alternatively, the motion correction may employed within the reconstruction of the images from the profiles. Further. the motion detection may be employed to pause the scan when motion is detected and to resume data acquisition after motion. In another further example the motion detected may be employed stop the data acquisition and re-acquire the data.

The invention also pertains to a computer programme comprising instructions for selecting an imaging zone to be tomographically imaged
acquiring tomographic image-data from the selected imaging zone in a reference coordinate system,
receiving dynamic image information registered in a dynamic camera system's image coordinate frame,
projecting at least a portion of the selected imaging zone from the reference coordinate frame onto the image coordinate-frame and deriving motion information from the registered dynamic image information in the projected selected imaging zone.

When installed into the tomographic imaging system's control processor, the tomographic imaging system is enabled to avoid motion that may be in the range of the dynamic camera system but not in the (imaging) zone of interest in motion correction of the tomographic image information. That is, any motion that may be in the range of the dynamic camera system, but not or unlikely to be confounding the image quality of the tomographic image, will not be taken into account for motion detection. The invention obviates the need to (e.g. manually) restrict the camera range to the imaging zone and its close surroundings. Accordingly, when the computer programme is installed in the control processor, the tomographic imaging system is enabled to carry-out motion detection in a more reliable manner. The computer programme of the invention may be provided on a data carrier such as a CD-ROM or a USB-stick. Alternatively, the computer programme of the invention may be downloaded from a data-network such as the world-wide web or cloud-based.

These and other aspects of the invention will be elucidated with reference to the embodiments described hereinafter and with reference to the accompanying drawing.

DETAILED DESCRIPTION OF THE EMBODIMENTS

Figure 1:
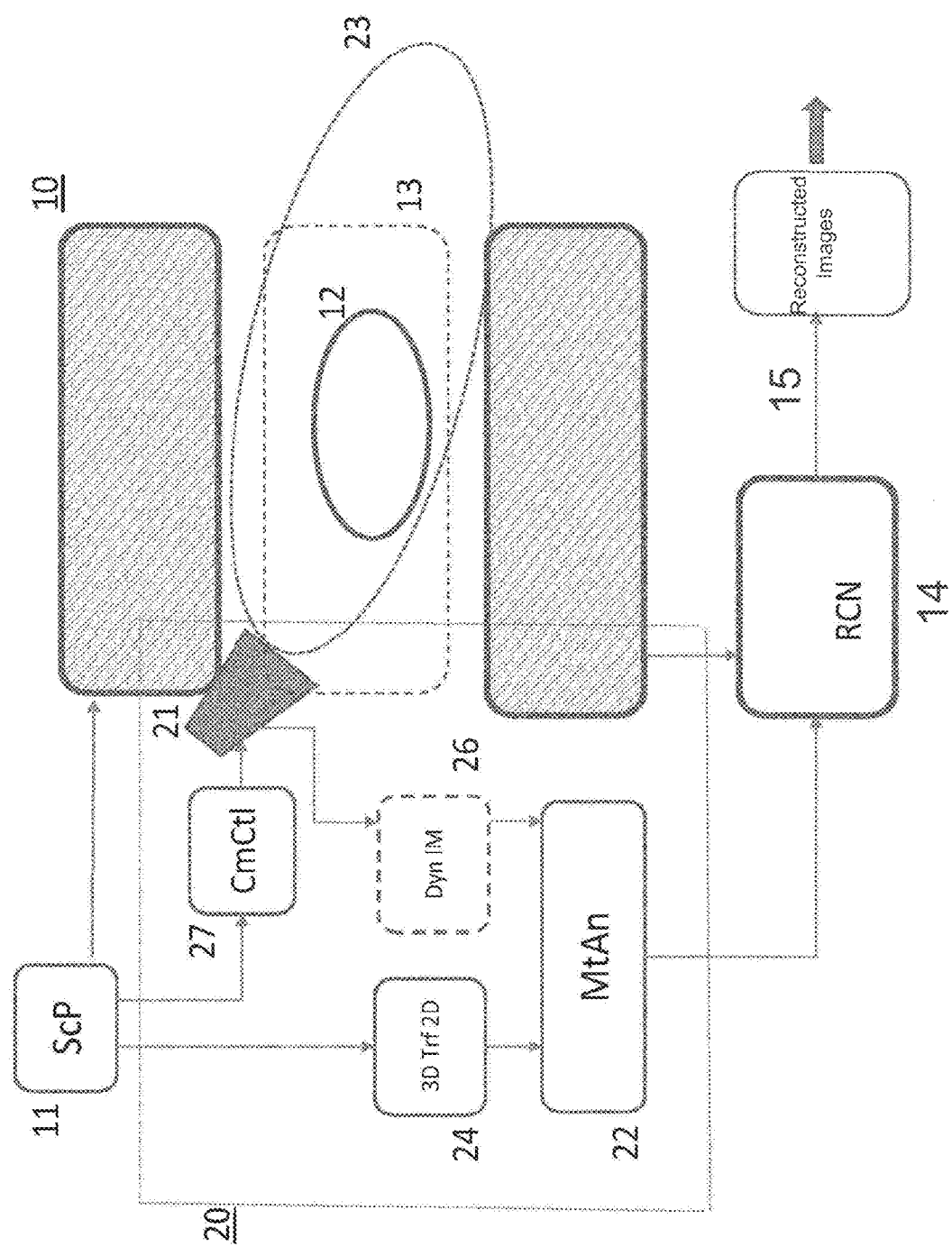
FIG. 1 shows a schematic side elevation of the tomographic imaging system of the invention.

FIG. 1 shows a schematic side elevation of the tomographic imaging system of the invention. The tomographic imaging system's support 10 defines an examination zone 13 in which a subject, e.g. a patient to be examined, can be placed for imaging. By way of the scan plan control 11, the imaging zone 12, i.e. the portion of the subject to be imaged, is defined in the reference coordinate-frame and the tomographic imaging system controlled to acquire the tomographic image data from that selected imaging zone 12. The motion detection system 20 includes the dynamic camera system 21 and the motion analyser 22. The camera range 23 of the dynamic camera extends into the examination region 13 and includes the selected imaging zone, but may extend beyond the imaging zone 12 and even beyond the examination region 13. The selected imaging region is applied to the camera control 27 to control the dynamic camera 21 to capture the selected imaging zone 12 in its range 23. The dynamic image information 26 of the dynamic camera system is applied to the motion analyser 22. When the dynamic camera system is fixedly mounted to the support 10, then there is an inherent geometric transformation between the reference coordinate system onto the imaging coordinate-frame of the dynamic camera system itself. When the dynamic camera system is moveable with respect to the support, then such a geometrical transformation may need to be calibrated each time the relative orientation and position of the dynamic camera system are changed. The arithmetic unit 24, e.g. a computational processor is configured or programmed to compute positions in the selected imaging zone in the reference coordinate frame onto the image coordinate frame of the dynamic camera system 21. That is, positions in the selected imaging zone are projected onto image pixel coordinates of the dynamic images. The motion analyser 22 is further configured to detect motion in the dynamic images, i.e. change of position and orientation of features in the dynamic image. Moreover, the motion analyser 22 is configured to distinguish in the image coordinate-frame detected motion to be in or near the selected imaging zone 12. Then, the detected motion found to be in the imaging zone is applied to a reconstructor 14 of (or for) the tomographic imaging system. The reconstructor 14 also receives tomographic image data from the tomographic imaging system 10 (e.g. k-space profiles or attenuation profiles), and provide reconstructed images at an output 15. In the image reconstructed form the k-space profiles or attenuation profiles, account is taken of the motion detected in or near the imaging zone and the reconstructed image is corrected or compensated for such motion. Alternatively, the motion detection data may be passed to the scan control unit to pause/resume the image data acquisition process. The reconstructed image has a low level of residual (if any) motion artefacts and hence has a good diagnostic quality.

Figure 2:
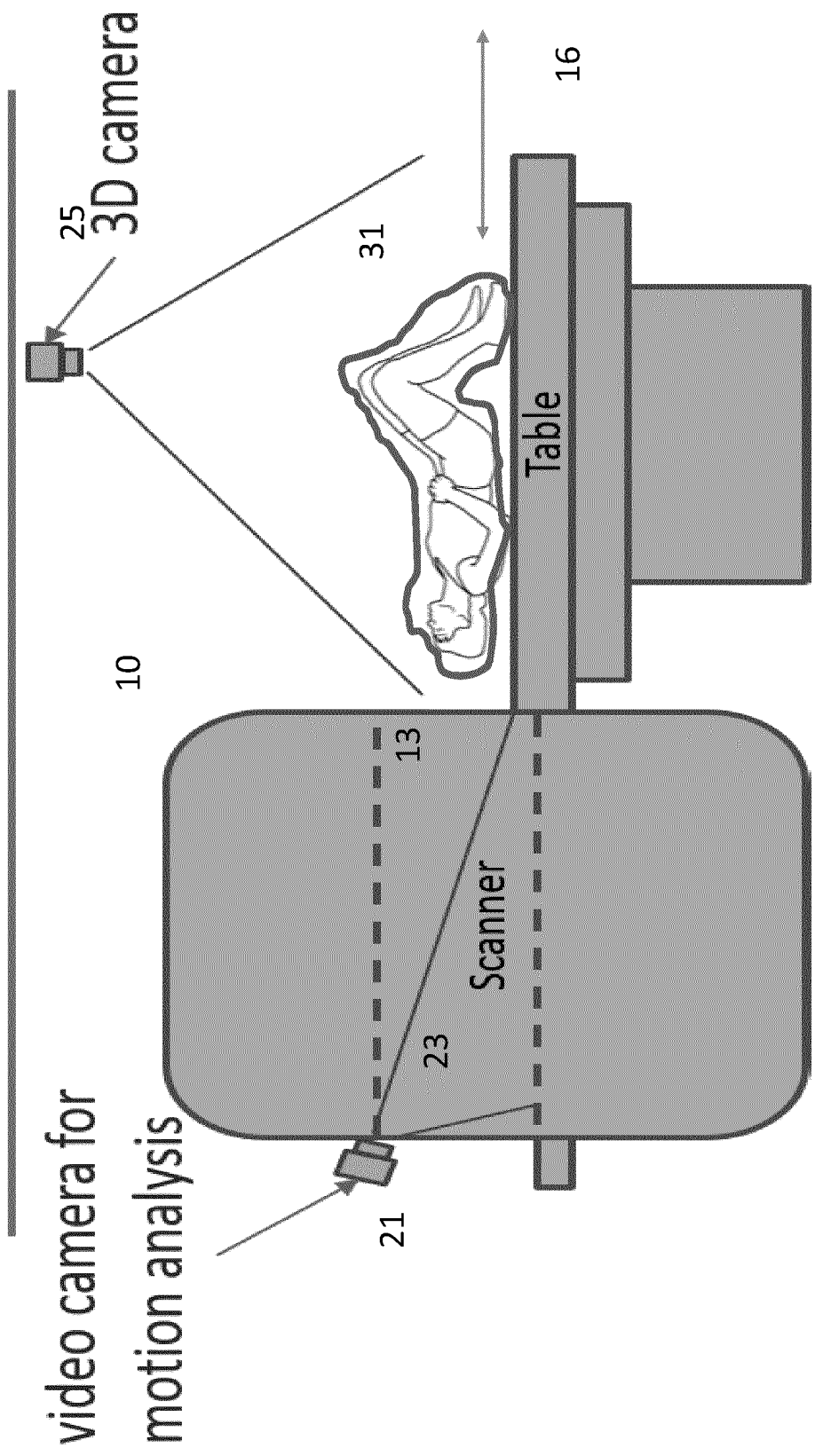
FIG. 2 and FIG. 3 show schematic side elevations of embodiments of the tomographic imaging system of the invention.
Figure 3:
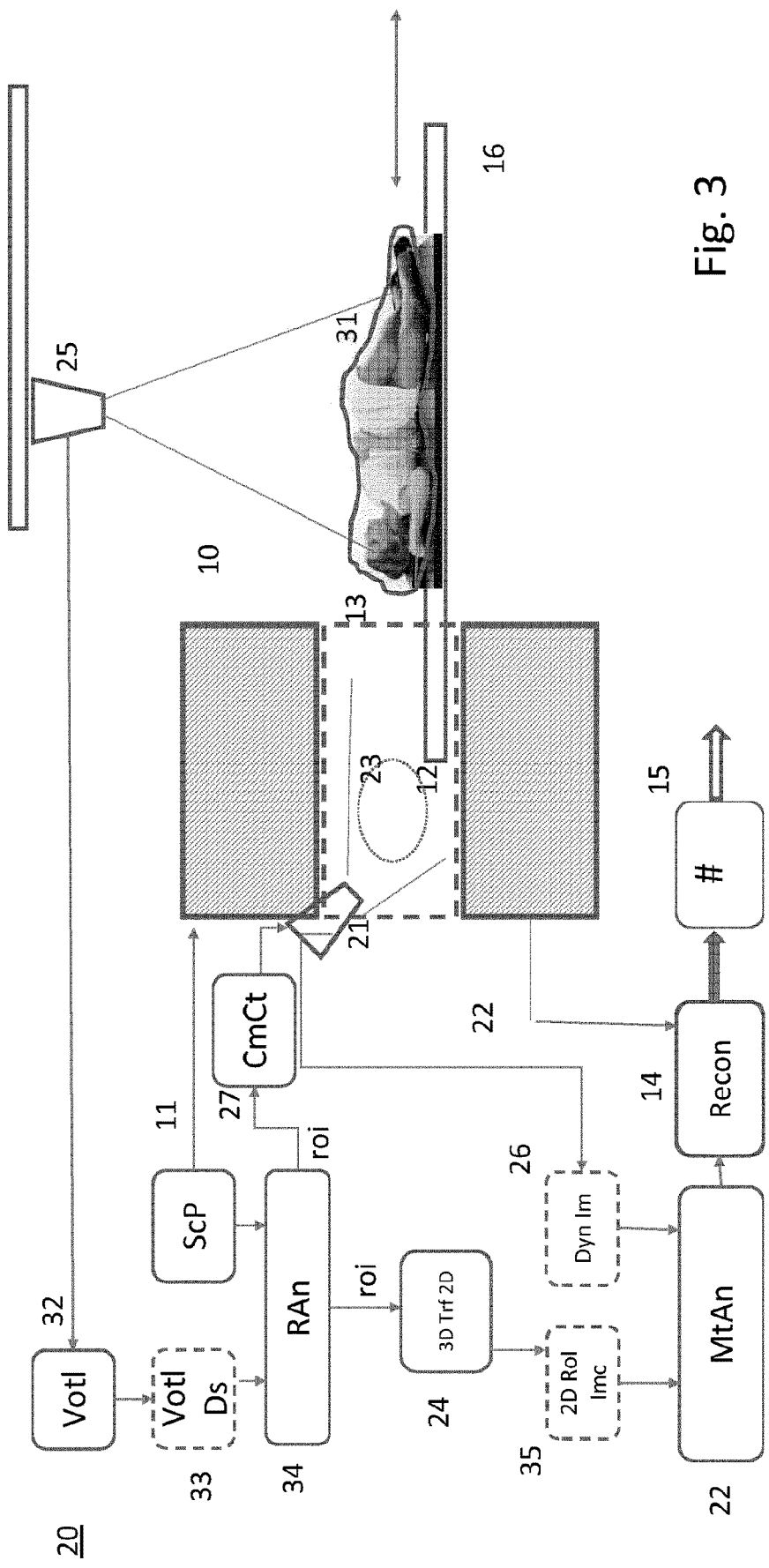

FIG. 2 and FIG. 3 show schematic side elevations of embodiments of the tomographic imaging system of the invention. FIG. 2 shows schematically an implementation of the tomographic imaging system of the invention that employs a volumetric outline 31 of the patient to be examined. As shown in FIG. 2, the volumetric outline may be acquired while the patient to be examined is still outside of the examination region 13. To that end, a 3D camera 25 is mounted e.g. to the ceiling of the examination room such that the patient to be examined is in the 3D camera's view when the patient to be examined is positioned on the patient carrier 16, but not yet in position in the examination region 13 of the tomographic imaging system. The 3D camera 25 is calibrated in the reference coordinate frame. When the volumetric outline has been acquired by the 3D cameras 25, the patient support 16 with the patient to be examined may be moved into the examination region 13 as indicated by the double arrow.

The tomographic imaging system of FIG. 3 makes use of the volumetric outline 31 of the patient to be examined. The 3D camera 25 applies its output in the form of 3D camera data to an volumetric outline unit 32 that is configured in software to compute the volumetric outline 31 of the patient to be examined from the 3D camera data in the reference coordinate frame as a volumetric outline data set 33. The region analyser 34 analyses the zone-of-interest formed by portion(s) of the volumetric outline 31 in the reference coordinate-frame that falls in the selected imaging zone 12 when the patient carrier 16 is in its final position and the imaging zone contains the portion of the anatomy of the patient to be examined that is to be imaged. To that end the region analyser 34 is provided with the position data of the patient to be examined. The region analyser 34 also receives information on the selected imaging zone 12 that is associated with the selected scan protocol from the scan plan control 11. That is, the region analyser 34 computes in the reference coordinate-frame of the tomographic imaging system the volumetric zone-of-interest formed by the part(s) of the volumetric outline 31 that fall(s) within the imaging zone 12 when the patient to be examined is in its position to be imaged. This zone-of-interest of the volumetric outline 31 within the imaging zone 12 is fed to the camera control 27 to steer the camera 21 to focus on that part of the volumetric outline. The zone-of interest in the reference coordinate frame is then applied to the geometric transformation onto the image coordinate frame by the arithmetic unit 24. That is the volumetric zone-of-interest derived by the region analyser 34 is projected onto the 2D image coordinate-frame, as the region-of-interest in the image pixel coordinates. To that end the arithmetic unit 24 is configured in software to transform the zone of interest of the volumetric outline 31 within the imaging zone from the support or gantry of the tomographic imaging system 10 onto the image coordinate-frame of the camera system. The 2D region-of-interest 35 of the volumetric outline is applied to the motion analyser 22. Also the dynamic image information 26 from the camera 21 is applied to the motion analyser 22. The motion analyser 22, by comparing the 2D region-of-interest with the dynamic image information determine overlap of the dynamic image information with the 2D region-of-interest. This overlap determines the portion of detected motion in the dynamic image information that may be of negative effect to the diagnostic image quality of the magnetic resonance image and needs correction either of the acquired data profiles or in the reconstruction 14. From the determined motion there may be derived motion corrections that may be applied to correct the tomographic image data. Alternatively, the motion corrections may be employed for motion correction in the reconstruction of the tomographic images from the tomographic image data, r to pause, resume, stop or repeat data acquisition.

The invention claimed is:

1. A tomographic imaging system, comprising:
   a support carrying a tomographic image-data acquisition system and defining a reference coordinate frame;
   a scan plan control to set the tomographic image-data acquisition system to acquire tomographic image-data from a selected imaging zone in the reference coordinate system;
   a motion detection system to detect movement and comprising:
   a dynamic camera system to receive dynamic image information registered in the image coordinate frame of the dynamic camera system;
   an arithmetic unit configured to transform the selected imaging zone from the reference coordinate frame to the image-coordinate-frame;
   a motion analyser to derive motion information from the registered dynamic image information in the transformed selected imaging zone, wherein the motion detection system has access to a volumetric outline, from survey scan-data or from the dynamic camera system, including the selected imaging zone in the reference coordinate-frame;
   a region-analyser to determine within the selected imaging zone in the reference coordinate-frame a zone of interest of the volumetric outline within the selected imaging zone, wherein the arithmetic unit configured to transform the zone-of-interest from the reference coordinate system onto the image coordinate-frame of the dynamic camera system, thus determining a transformed zone of interest; and
   a camera control to set the acquisition of the dynamic camera system to acquire dynamic image information from at least the determined transformed zone of interest, wherein the motion-analyser is set to predominantly derive motion from the dynamic image information from the transformed zone of interest.

2. The tomographic imaging system of claim 1, further including a gantry that defines the reference coordinate frame.

3. The tomographic imaging system of claim 1, wherein the dynamic camera system is mounted to the support such that at least a portion of the selected imaging zone is in the dynamic camera system's range.

4. The tomographic imaging system of claim 1, wherein the motion detection system is provided with a depth-camera to acquire the volumetric outline.

5. The tomographic imaging system of claim 3, wherein the depth-camera is part of the dynamic camera system.

6. The tomographic imaging system of claim 1, wherein the arithmetic unit is further configured to transform the derived or acquired volumetric outline to the reference coordinate-frame defined by the support.

7. A method of motion detection of a subject during tomographic imaging, the method comprising:
   selecting an imaging zone to be tomographically imaged;
   acquiring tomographic image-data from the selected imaging zone in a reference coordinate system;
   receiving dynamic image information registered in a dynamic camera system's image coordinate frame;
   projecting at least a portion of the selected imaging zone from the reference coordinate frame onto the image coordinate frame;
   deriving motion information from the registered dynamic image information in the projected selected imaging zone;
   accessing in the reference coordinate frame a volumetric outline of the subject to be tomographically imaged;
   determining a zone of interest of one or more portions of interest of the volumetric outline within the selected imaging zone;
   transforming the zone of interest from the reference coordinate frame onto the image coordinate frame of the dynamic camera system, thus determining a transformed zone of interest; and
   deriving motion from the dynamic image information predominantly in the transformed zone of interest.

8. The method of claim 7, wherein the dynamic camera system is mounted to the support such that at least a portion of the selected imaging zone is in the dynamic camera system's range.

9. The method of claim 7, wherein the motion detection system is provided with a depth-camera to acquire the volumetric outline.

10. The method of claim 9, wherein the depth-camera is part of the dynamic camera system.

11. The method of claim 7, further comprising transforming the derived or acquired volumetric outline to the reference coordinate frame defined by the support.

12. A tangible, non-transitory computer readable medium that stores instructions, which when executed by a processor, cause the processor to:
   select an imaging zone to be tomographically imaged acquiring tomographic image-data from the selected imaging zone in a reference coordinate system;
   receive dynamic image information registered in a dynamic camera system's image coordinate frame;
   project at least a portion of the selected imaging zone from the reference coordinate frame onto the image coordinate frame;
   derive motion information from the registered dynamic image information in the projected selected imaging zone;
   access in the reference coordinate-frame a volumetric outline of the subject to be tomographically imaged;
   determine a zone of interest of one or more portions of interest of the volumetric outline within the selected imaging zone;
   transform the zone of interest from the reference coordinate frame onto the image coordinate frame of the dynamic camera system, thus determining a transformed zone of interest; and
   derive motion from the dynamic image information predominantly in the transformed zone of interest.

13. The tangible, non-transitory computer readable medium of claim 12, further including a gantry that defines the reference coordinate frame.

14. The tangible, non-transitory computer readable medium of claim 12, wherein the dynamic camera system is mounted to the support such that at least a portion of the selected imaging zone is in the dynamic camera system's range.

15. The tangible, non-transitory computer readable medium of claim 12, wherein the motion detection system is provided with a depth-camera to acquire the volumetric outline.

16. The tangible, non-transitory computer readable medium of claim 14, wherein the depth-camera is part of the dynamic camera system.

17. The tangible, non-transitory computer readable medium of claim 12, wherein the processor is further configured to transform the derived or acquired volumetric outline to the reference coordinate-frame defined by the support.

* * * * *